United States Patent
Jensen et al.

(10) Patent No.: US 7,033,624 B2
(45) Date of Patent: Apr. 25, 2006

(54) **PREVENTATIVE AND TREATMENT EFFECTS OF *MORINDA CITRIFOLIA* ON OSTEOARTHRITIS AND ITS RELATED CONDITIONS**

(75) Inventors: Claude Jarakae Jensen, Cedar Hills, UT (US); Afa Kehaati Palu, Orem, UT (US)

(73) Assignee: Morinda, Inc., Provo, UT (US)

( * ) Notice: Subject to any disclaimer, the term of this patent is extended or adjusted under 35 U.S.C. 154(b) by 0 days.

(21) Appl. No.: 10/285,359

(22) Filed: Oct. 31, 2002

(65) Prior Publication Data

US 2003/0108631 A1    Jun. 12, 2003

Related U.S. Application Data

(60) Provisional application No. 60/335,343, filed on Nov. 2, 2001.

(51) Int. Cl.
*A61K 35/78* (2006.01)
(52) U.S. Cl. .................................. 424/777; 424/725
(58) Field of Classification Search ............ 424/195.1, 424/725, 777
See application file for complete search history.

(56) References Cited

U.S. PATENT DOCUMENTS 5,595,756 A * 1/1997 Bally et al. ................. 424/450

OTHER PUBLICATIONS

Lane, K., e.d.; The Merck Manual, Seventeenth Edition, 1999, Merck & Company, pp. 449-451.*
Webb, D. Noni Juice Advice; Prevention magazine, Aug. 2000, vol. 52, p. 66, ProQuest [online] [pp. 1-2 of web site print-out retrieved on Jan. 30, 2004].*

* cited by examiner

*Primary Examiner*—Patricia Leith
(74) *Attorney, Agent, or Firm*—Michael F. Krieger; Kirton & McConkie

(57) ABSTRACT

The present invention embraces methods for improved treatment of osteoarthritis by featuring a naturaceutical formulation or composition for treating osteoarthritis and its associated or related conditions. The present invention further features methods of treating osteoarthritis and its related conditions. In particular, the present invention relates to providing a treatment for osteoarthritis that includes one or more processed products described below as derived and produced from the Indian Mulberry plant, scientifically known as *Morinda citrifolia L.*

4 Claims, No Drawings

PREVENTATIVE AND TREATMENT EFFECTS OF *MORINDA CITRIFOLIA* ON OSTEOARTHRITIS AND ITS RELATED CONDITIONS

RELATED APPLICATION

This application claims priority to U.S. Provisional Application Ser. No. 60/335,343 filed Nov. 2, 2001, and entitled, "Methods for Treating Osteoarthritis."

BACKGROUND

1. Field of the Invention

The present invention relates to methods and naturaceutical formulations and substances for treating and preventing Osteoarthritis and its associated symptoms and conditions. Specifically, the present invention relates to processed *Morinda citrifolia* product-based methods and naturaceutical formulations and substances for treating pre-existing Osteoarthritis, as well as to *Morinda citrifolia*-based methods and naturaceutical formulations and substances for preventing the onset or reducing the onset potential of future or additional osteoarthritis developments. The present invention is particularly suited for treatment and prevention of Osteoarthritis as commonly experienced in mammals, and particularly humans.

2. Background of the Invention and Related Art

Osteoarthritis is a type of arthritis that is caused by the breakdown of cartilage with eventual loss of the cartilage of the joints. Cartilage is a protein substance that serves as a cushion between the bones of the joints. Osteoarthritis is also known as degenerative arthritis. Among the over 100 different types of arthritis conditions, osteoarthritis is the most common, affecting over 15 million people in the United States. Before age 45, osteoarthritis occurs more frequently in males. After age 55 years, it occurs more frequently in females. In the United States, all races appear equally affected. A higher incidence of osteoarthritis typically exists in the Japanese population, while South African blacks, East Indians and southern Chinese have lower rates.

Osteoarthritis usually affects the hands, feet, spine, and large weight-bearing joints, such as the hips and knees. Most cases of osteoarthritis have no known cause, and are called primary osteoarthritis. When the cause of the osteoarthritis is known, the condition is called secondary osteoarthritis.

Primary osteoarthritis is mostly related to aging. With aging, the water content of the cartilage increases and the protein makeup of cartilage degenerates. Repetitive use of the joints over the years irritates and inflames the cartilage, causing joint pain and swelling. Eventually, cartilage begins to degenerate by flaking or forming tiny crevasses. In advanced cases, there is a total loss of the cartilage cushion between the bones of the joints. Loss of cartilage cushion causes friction between the bones, leading to pain and limitation of joint mobility. Inflammation of the cartilage can also stimulate new bone outgrowths (spurs) that form around the joints. Osteoarthritis occasionally can be found in multiple members of the same family, implying a genetic basis for this condition.

Treating the pain associated with osteoarthritis is a common challenge for physicians. Nonsteroidal anti-inflammatory drugs (NSAIDs) have long been used to manage this disease. NSAIDs are particularly useful in treating joint pain, muscle pain, and joint swelling. There are many different types of NSAIDs, including aspirin and other salicylates. Examples include ibuprofen,(e.g., Advil®, Motrin®, Nuprin®) naproxen, sulindac, diclofenac, piroxicam, ketoprofen, diflunisal, nabumetone, etodolac, oxaprozin, and indomethacin. Popular NSAIDs include: ibuprofen, naproxen and aspirin.

The adverse side effects of NSAIDs, however, are well known and includes gastrointestinal and renal complications. In patients who take NSAIDs regularly, upper endoscopic examinations have shown a 15 to 30 percent prevalence of ulcers in the stomach or duodenum. The major side effects of NSAIDs are gastrointestinal related. For example, between 10 and 50 percent of the patients being treated with NSAIDs suffer side effects such as diarrhea, heartburn, increased abdominal pain, and upset stomach. A significant percentage of these patients also develop ulcers in the stomach and upper GI tract, which can lead to internal bleeding and other complications.

Since significant numbers of patients taking NSAIDs were suffering from an increased risk of ulceration in the stomach, researchers began investigating the mechanisms by which NSAIDs inhibit and prevent inflammation. Researchers knew that in most instances, inflammation in human tissues (and the pain associated with it) is related to the conversion of arachidonic acid (a molecule present in the majority of human body cells) into a prostaglandin in the cells of the tissue. The conversion arachidonic acid to a prostaglandin requires the presence of an enzyme known as cyclooxygenase (COX). NSAIDS were known to inhibit the COX enzyme and thereby prevent or reduce inflammation.

As researchers studied the COX inhibitory activity of NSAIDs, they discovered that there are in fact two different COX enzymes: COX-1 and COX-2. COX-1 and COX-2 are isoforms of cyclooxygenase, both of which catalyze the first two steps in the biosynthesis from arachidonic acid to the prostaglandins. The difference is that COX-1 is constitutive and COX-2 is inducible. COX-1 presents in nearly all parts of body at a constant level to produce the prostaglandins to line the stomach, maintain normal renal function, prevent platelet aggregation. On the other hand, COX-2 is normally absent from body and induced at the infected sites by those associated with inflammation such as bacterial polysaccharide and cytokines, interleukin-1, -2, and tumor necrosis factor. Once induced, COX-2 produces large amount of prostaglandins which lower the pain threshold (causes pain), raise the set point of the temperature-regulating center (causes fever), cause peripheral vasodilatation with local redness and edema formation. Therefore, the inhibition of COX-1 will lead to a series of side effects such as gastrointestinal ulceration and bleeding, renal damage, and platelet dysfunction, while the selective inhibition of COX-2 offers the advantage of inhibition of inflammation without disturbing normal body functions.

Researchers have discovered that most "first generation" NSAIDs inhibit the enzymatic activities of both COX-1 and COX-2, and do not selectively inhibit COX-2 enzyme. Therefore, when a patient takes a typical NSAID, COX-2 is inhibited and inflammation is thereby reduced, but COX-1 is also inhibited.

In order to provide relief from inflammation associated with COX-2 without losing the COX 1 enzyme, drug companies have attempted to produce drugs that selectively inhibit COX-2 without inhibiting COX-1. Selective COX-2 inhibition drugs have been developed and made available to the public for several years now. These selective COX-2 inhibition drugs were initially thought to be of special benefit to arthritis sufferers and those with chronic pain due to inflammation.

Even though selective COX-2 inhibition drugs have been reported to be a success, there are doubts about manufacturers' claims that selective COX-2 inhibition drugs are "safer" than non-selective COX inhibitors. Some of the side effects associated with non- with non-selective COX inhibitors are also found to be associated with selective COX-2 inhibition drugs. More importantly, people using selective COX-2 inhibition drugs have been shown to have four times the risk of suffering a heart attack than those taking traditional, non-selective NSAIDs.

By not inhibiting the COX-1 enzyme, selective COX-2 inhibition drugs were intended to be safer than the non-selective NSAIDs. However, there appears to be considerable risk associated with prolonged use of selective COX-2 inhibition drugs. At present, it is not known if the cause of the increased risk of heart attack associated with COX-2 inhibition is directly related to the inhibiting properties of the drug or if the increased risk of heart attack is the result of some other interaction with these particular selective COX-2 inhibition drugs. Ironically, some patients taking selective COX-2 inhibition drugs who are concerned with increased risk of heart attacks are attempting to reduce the risk by taking aspirin and other traditional non-selective NSAIDs along with the selective COX-2 inhibition drugs.

Other problems associated with the selective COX-2 inhibition drugs further complicate the ability of healthcare providers to easily and effectively treat patients suffering from inflammation. For example, in most cases selective COX-2 inhibition drugs are available by prescription only. Thus, in order to obtain these drugs, the patients are required to visit the doctor and receive a diagnosis that calls for these prescription drugs. After the visit, the patient must, of course, obtain the drugs from the pharmacy with the associated inconvenience that this process entails. Obtaining prescription drugs is much more complicated than buying over the counter pharmaceuticals or remedies and the cost of the drugs is significant.

Another disadvantage associated with selective COX-2 inhibition drugs is that they are, at present, not approved for pediatric use. Selective COX-2 inhibition drugs are unavailable to children who unfortunately may be more distressed than an adult would be by the unpleasant side effects associated with non-selective NSAIDs. Approval of pediatric selective COX-2 inhibition drugs may take several years, if such drugs are approved at all.

Other disadvantages of selective COX-2 inhibition drugs presently available also include the dangers of uncertain drug interaction for patients who are taking other medications in addition to selective COX-2 inhibition drugs. Also, pregnant women cannot take the selective COX-2 inhibition drugs during certain periods of fetal development. It has been determined that selective COX-2 inhibition drugs have teratogenic effects on fetuses. Additionally, potential harm could come to the patient if a COX 2 selective inhibitor is taken at a time when the patient is not properly hydrated.

While improvements in alternatives for treating patients with osteoarthritis have occurred in recent decades, researchers are continually attempting to obtain improved methods of treatment. Accordingly, it would be an improvement in the art to augment or even replace the treatments currently used with other treatments to provide increased results in treating osteoarthritis and its associated symptoms without negative side effects, such as gastrointestinal discomfort and other side effects. It would also be an improvement to provide a method and formulation that reduces inflammation and the pain associated with inflammation and at the same time limits the adverse side effects, such as those associated with selective COX-2 inhibition drugs of the prior art.

SUMMARY AND OBJECTS OF THE INVENTION

Based on the foregoing, the present invention seeks to advance prior art formulations and methods for treating osteoarthritis by providing a unique naturaceutical formulation or composition, a unique topical dermal composition, and a unique systemically administered composition for treating osteoarthritis and its associated conditions that is devoid of many of the deficiencies described in the above-identified prior art osteoarthritis treatments.

Therefore, it is an object of some embodiments of the present invention to provide a naturaceutical formulation or composition, and specifically a naturaceutical formulation or composition comprising a processed *Morinda citrifolia* product, for treating osteoarthritis and its related conditions.

It is another object of some embodiments of the present invention to provide a processed *Morinda citrifolia*-based naturaceutical formulation for treating existing osteoarthritis.

It is still another object of some embodiments of the present invention to provide a processed *Morinda citrifolia*-based naturaceutical formulation for reducing, inhibiting, or preventing additional degeneration of cartilage, and particularly the degeneration of the protein makeup of cartilage.

It is still another object of some embodiments of the present invention to provide a naturaceutical formulation comprising processed *Morinda citrifolia* product in one or more forms, including fruit juice, fruit juice concentrate, puree juice, puree juice concentrate, dietary fiber, or oil or oil extract.

It is still another object of some embodiments of the present invention to provide a naturaceutical formulation that may be administered to a patient via one of several methods, including orally, transdermally, intravenously, or systemically.

It is still another object of some embodiments of the present invention to provide a processed *Morinda citrifolia*-based naturaceutical formulation for treating conditions and symptoms associated with osteoarthritis.

In accordance with the foregoing objects, and in accordance with the embodiments as broadly described and claimed herein, the present invention embraces methods for improved treatment of osteoarthritis by featuring a naturaceutical formulation or composition for treating osteoarthritis and its associated or related conditions. The present invention further features methods of treating osteoarthritis and its related conditions. In particular, the present invention relates to providing a treatment for osteoarthritis that includes one or more processed products described below as derived and produced from the Indian Mulberry plant, scientifically known as *Morinda citrifolia* L.

Implementation of the present invention takes place in association with the utilization of the naturaceutical formulation comprising one or more processed *Morinda citrifolia* products to treat osteoarthritis and other similar conditions.

In several exemplary embodiments, the processed products may comprise processed *Morinda citrifolia* fruit juice and/or fruit juice concentrate, processed *Morinda citrifolia* puree juice and/or puree juice concentrate, processed *Morinda citrifolia* dietary fiber, and processed *Morinda citrifolia* oil or oil extract. In addition, the processed *Morinda citrifolia* products may be embodied in the form of a dietary supplement (powder or liquid), an ointment, a lotion, or in any other known form.

As stated, osteoarthritis, also known as degenerative arthritis, is a type of arthritis that is caused by the breakdown of cartilage with eventual loss of the cartilage of the joints. A treatment in the form of a dietary supplement, an ointment, a lotion, or another form that includes juice is used to treat osteoarthritis. The amount used per treatment may depend on various factors, including the degree of the osteoarthritis, the physical characteristics of the patient, etc. The use of a processed *Morinda citrifolia* product as taught and described herein has proven to be advantageous in treating osteoarthritis and other related conditions by providing significant immediate relief, reducing the onset potential of additional debilitating conditions, reducing the degenerative rate of cartilage and the proteins existing in cartilage, and improving the overall conditions of arthritis sufferers. Moreover, the processed *Morinda citrifolia* products comprise antibacterial properties that are particularly useful in fighting infections.

The treatment for osteoarthritis, which includes administration of the naturaceutical formulation comprising one or more processed *Morinda citrifolia* products, functions to reduce the pain and attending disability of the individual, as well as to increase the overall quality of life of an individual with osteoarthritis. In one embodiment, the treatment is taken regularly. One of the primary benefits of the present invention naturaceutical formulation that comprises one or more processed *Morinda citrifolia* products is its ability to achieve beneficial results in treating the chronic degenerative disease osteoarthritis.

In still another embodiment, the present invention features a method of administering a naturaceutical formulation comprising one or more processed *Morinda citrifolia* products concurrently with an osteoarthritis medication. Taking the *Morinda citrifolia*-based naturaceutical concurrently with an osteoarthritis medication functions to increase the efficacy of the an osteoarthritis medication.

The present invention *Morinda citrifolia*-based formulations and compositions described herein also have beneficial Cyclooxygenase-1 and 2 (COX-1 and COX-2) implications that further contribute to treatment of osteoarthritis. As such, the present invention further features a naturaceutical formulation and method for reducing and limiting inflammation of cartilage in the joints and the pain associated with such inflammation. One embodiment of the present invention uses a selective COX-2 inhibitor as an anti-inflammatory agent where use of the selective COX-2 inhibitor does not result in the unpleasant side effects associated with NSAIDs and selective COX-2 inhibition drugs presently available.

While the methods and processes of the present invention have proven to be particularly useful in the area of osteoarthritis, those skilled in the art can appreciate that the methods can be used in a to treat a variety similar disorders or symptoms, such as degenerative back pain, diabetes, or other conditions.

DETAILED DESCRIPTION OF THE PREFERRED EMBODIMENTS

It will be readily understood that the components of the present invention, as generally described herein, could be arranged and designed in a wide variety of different configurations. Thus, the following more detailed description of the embodiments of the system and method of the present invention is not intended to limit the scope of the invention, as claimed, but is merely representative of the presently preferred embodiments of the invention.

The present invention describes and features formulations and methods for treating osteoarthritis and its related conditions, and particularly to the inhibition, blocking, and/or prevention of protein makeup and subsequent cartilage degeneration in the body of a mammal, through the prophylactic administration of a naturaceutical formulation or composition comprising one or more processed *Morinda citrifolia* products.

The presently preferred embodiments of the invention will be best understood by separating the description into sections, the first pertaining to a general discussion regarding *Morinda citrifolia*, including its origins, processing techniques, and health benefits, and the methods employed to produce and manufacture the processed *Morinda citrifolia* products used as key ingredients in the naturaceutical formulations described herein; the second being a more detailed and specific discussion on the *Morinda citrifolia*-based methods and naturaceutical formulations or compositions used to treat and inhibit or prevent osteoarthritis and its associated symptoms or conditions, such treatment methods involving the prophylactic administration of the processed *Morinda citrifolia* product-based formulations as described herein; and the third being Cyclooxygenase-1 and 2 (or COX-1 and COX-2) implications. Examples of experimental studies and the results obtained are also provided herein.

General Discussion of *Morinda citrifolia* and the Methods Used to Produce Processed *Morinda citrifolia* Products The Indian Mulberry or Noni plant, known scientifically as *Morinda citrifolia L.* (hereinafter "*Morinda citrifolia*"), is a shrub or small tree up to 10 m in height. The leaves are oppositely arranged with an elliptic to ovate form. The small white flowers are contained in a fleshy, globose, head-like cluster. The fruits are large, fleshy, and ovoid. At maturity, they are creamy-white and edible, but have an unpleasant taste and odor. The plant is native to Southeast Asia and has spread in early times to a vast area from India to eastern Polynesia. It grows randomly in the wild, and it has been cultivated in plantations and small individual growing plots. The *Morinda citrifolia* flowers are small, white, three to five lobed, tubular, fragrant, and about 1.25 cm long. The flowers develop into compound fruits composed of many small drupes fused into an ovoid, ellipsoid or roundish, lumpy body, with waxy, white, or greenish-white or yellowish, semi-translucent skin. The fruit contains "eyes" on its surface, similar to a potato. The fruit is juicy, bitter, dull-yellow or yellowish-white, and contains numerous red-brown, hard, oblong-triangular, winged 2-celled stones, each containing four seeds.

When fully ripe, the fruit has a pronounced odor like rancid cheese. Although the fruit has been eaten by several nationalities as food, the most common use of the *Morinda citrifolia* plant was as a red and yellow dye source. Recently, there has been an interest in the nutritional and health benefits of the *Morinda citrifolia* plant, further discussed below.

Because the *Morinda citrifolia* fruit is for all practical purposes inedible, the fruit must be processed in order to make it palatable for human consumption and included in the naturaceuticals used to treat osteoarthritis. Processed *Morinda citrifolia* fruit juice can be prepared by separating seeds and peels from the juice and pulp of a ripened *Morinda*

*citrifolia* fruit; filtering the pulp from the juice; and packaging the juice. Alternatively, rather than packaging the juice, the juice can be immediately included as an ingredient in another food product, frozen or pasteurized. In some embodiments, the juice and pulp can be pureed into a homogenous blend to be mixed with other ingredients. Other process include freeze drying the fruit and juice. The fruit and juice can be reconstituted during production of the final juice product. Still other processes include air drying the fruit and juices, prior to being masticated.

The present invention utilizes the fruit juice, the puree, and the oil extracted from the *Morinda Citrifolia* plant. In a currently preferred process of producing *Morinda citrifolia* fruit juice, the fruit is either hand picked or picked by mechanical equipment. The fruit can be harvested when it is at least one inch (2–3 cm) and up to 12 inches (24–36 cm) in diameter. The fruit preferably has a color ranging from a dark green through a yellow-green up to a white color, and gradations of color in between. The fruit is thoroughly cleaned after harvesting and before any processing occurs.

The fruit is allowed to ripen or age from 0 to 14 days, with most fruit being held from 2 to 3 days. The fruit is ripened or aged by being placed on equipment so it does not contact the ground. It is preferably covered with a cloth or netting material during aging, but can be aged without being covered. When ready for further processing the fruit is light in color, from a light green, light yellow, white or translucent color. The fruit is inspected for spoilage or for excessively green color and hard firmness. Spoiled and hard green fruit is separated from the acceptable fruit.

The ripened and aged fruit is preferably placed in plastic lined containers for further processing and transport. The containers of aged fruit can be held from 0 to 30 days. Most fruit containers are held for 7 to 14 days before processing. The containers can optionally be stored under refrigerated conditions prior to further processing. The fruit is unpacked from the storage containers and is processed through a manual or mechanical separator. The seeds and peel are separated from the juice and pulp.

The juice and pulp can be packaged into containers for storage and transport. Alternatively, the juice and pulp can be immediately processed into a finished juice product. The containers can be stored in refrigerated, frozen, or room temperature conditions.

The *Morinda citrifolia* juice and pulp are preferably blended in a homogenous blend, after which they may be mixed with other ingredients, such as flavorings, sweeteners, nutritional ingredients, botanicals, and colorings. The finished juice product is preferably heated and pasteurized at a minimum temperature of 181° F. (83° C.) or higher up to 212° F. (100° C.).

Another product manufactured is *Morinda citrifolia* puree and puree juice, in either concentrate or diluted form. Puree is essentially the pulp a separated from the seeds and is different than the fruit juice product described herein.

Each product is filled and sealed into a final container of plastic, glass, or another suitable material that can withstand the processing temperatures. The containers are maintained at the filling temperature or may be cooled rapidly and then placed in a shipping container. The shipping containers are preferably wrapped with a material and in a manner to maintain or control the temperature of the product in the final containers.

The juice and pulp may be further processed by separating the pulp from the juice through filtering equipment. The filtering equipment may include a centrifuge decanter, a screen filter with a size from 1 micron up to 2000 microns, more preferably less than 500 microns, a filter press, reverse osmosis filtration., and any other standard commercial filtration devices. The operating filter pressure preferably ranges from 0.1 psig up to about 1000 psig. The flow rate preferably ranges from 0.1 g.p.m. up to 1000 g.p.m., and more preferably between 5 and 50 g.p.m. The wet pulp is washed and filtered at least once and up to 10 times to remove any juice from the pulp. The wet pulp typically has a fiber content of 10 to 40 percent by weight. The wet pulp may be pasteurized at a temperature of 181° F. (83° C.) minimum and then packed in drums for further processing or made into a high fiber product.

Drying may further process the wet pulp. The methods of drying may include freeze-drying, drum drying, tray drying, sun drying, and spray drying. The dried *Morinda citrifolia* pulp may include a moisture content in the range from 0.1 to 15 percent by weight and more preferably from 5 to 10 percent by weight. The dried pulp preferably has a fiber content in the range from 0.1 to 30 percent by weight, and more preferably from 5 to 15 percent by weight.

The high fiber product may include wet or dry *Morinda citrifolia* pulp, supplemental fiber ingredients, water, sweeteners, flavoring agents, coloring agents, and/or nutritional ingredients. The supplemental fiber ingredients may include plant based fiber products, either commercially available or developed privately. Examples of some typical fiber products are guar gum, gum arabic, soybean fiber, oat fiber, pea fiber, fig fiber, citrus pulp sacs, hydroxymethylcellulose, cellulose, seaweed, food grade lumber or wood pulp, hemicellulose, etc. Other supplemental fiber ingredients may be derived from grains or grain products. The concentrations of these other fiber raw materials typically range from 0 up to 30 percent, by weight, and more preferably from 10 to 30 percent by weight.

Typical sweeteners may include, but are not limited to, natural sugars derived from corn, sugar beet, sugar cane, potato, tapioca, or other starch-containing sources that can be chemically or enzymatically converted to crystalline chunks, powders, and/or syrups. Also sweeteners can consist of artificial or high intensity sweeteners, some of which are aspartame, sucralose, stevia, saccharin, etc. The concentration of sweeteners may be between from 0 to 50 percent by weight, of the formula, and more preferably between about 1 and 5 percent by weight.

Typical flavors can include, but are not limited to, artificial and/or natural flavor or ingredients that contribute to palatability. The concentration of flavors may range, for example, from 0 up to 15 percent by weight, of the formula. Colors may include food grade artificial or natural coloring agents having a concentration ranging from 0 up to 10 percent by weight, of the formula.

Typical nutritional ingredients may include vitamins, minerals, trace elements, herbs, botanical extracts, bioactive chemicals and compounds at concentrations from 0 up to 10 percent by weight. Examples of vitamins one can add to the fiber composition include, but are not limited to, vitamins A, B1 through B12, C, D, E, Folic Acid, Pantothenic Acid, Biotin, etc. Examples of minerals and trace elements one can add to the fiber composition include, but are not limited to, calcium, chromium, copper, cobalt, boron, magnesium, iron, selenium, manganese, molybdenum, potassium, iodine, zinc, phosphorus, etc. Herbs and botanical extracts include, but are not limited to, alfalfa grass, bee pollen, chlorella powder, Dong Quai powder, Ecchinacea root, Gingko Biloba extract, Horsetail herb, Indian mulberry, Shitake mushroom, spirulina seaweed, grape seed extract, etc. Typical bioactive chemicals may include, but are not limited to, caffeine, ephedrine, L-carnitine, creatine, lycopene, etc.

The juice and pulp can be dried using a variety of methods. The juice and pulp mixture can be pasteurized or enzymatically treated prior to drying. The enzymatic process begins with heating the product to a temperature between 75° F. and 135° F. It is then treated with either a single enzyme or a combination of enzymes. These enzymes include, but are not limited to, amylase, lipase, protease, cellulase, bromelin, etc. The juice and pulp may also be dried with other ingredients, such as those described above in connection with the high fiber product. The typical nutritional profile of the dried juice and pulp is 1 to 20 percent moisture, 0.1 to 15 percent protein, 0.1 to 20 percent fiber, and the vitamin and mineral content.

The filtered juice and the water from washing the wet pulp are preferably mixed together. The filtered juice may be vacuum evaporated to a brix of 40 to 70 and a moisture of 0.1 to 80 percent, more preferably from 25 to 75 percent. The resulting concentrated *Morinda citrifolia* juice may or may not be pasteurized. For example, the juice would not be pasteurized in circumstances where the sugar content or water activity was sufficiently low enough to prevent microbial growth. It is packaged for storage, transport and/or further processing.

The processed *Morinda citrifolia* product may also exist as a dietary fiber produced from the fruit puree. Still further, the processed *Morinda citrifolia* product may also exist in oil form, such as an oil extract. The *Morinda citrifolia* oil typically includes a mixture of several different fatty acids as triglycerides, such as palmitic, stearic, oleic, and linoleic fatty acids, and other fatty acids present in lesser quantities. In addition, the oil preferably includes an antioxidant to inhibit spoilage of the oil. Conventional food grade antioxidants are preferably used.

The *Morinda citrifolia* plant is rich in natural ingredients. Those ingredients that have been discovered include: (from the leaves): alanine, anthraquinones, arginine, ascorbic acid, aspartic acid, calcium, beta-carotene, cysteine, cystine, glycine, glutamic acid, glycosides, histidine, iron, leucine, isoleucine, methionine, niacin, phenylalanine, phosphorus, proline, resins, riboflavin, serine, beta-sitosterol, thiamine, threonine, tryptophan, tyrosine, ursolic acid, and valine; (from the flowers): acacetin-7-o-beta-d(+)-glucopyranoside, 5,7-dimethyl-apigenin-4'-o-beta-d(+)-galactopyranoside, and 6,8-dimethoxy-3-methylanthraquinone-1-o-beta-rhamnosyl-glucopyranoside; (from the fruit): acetic acid, asperuloside, butanoic acid, benzoic acid, benzyl alcohol, 1-butanol, caprylic acid, decanoic acid, (E)-6-dodeceno-gamma-lactone, (Z,Z,Z)-8,11,14-eicosatrienoic acid, elaidic acid, ethyl decanoate, ethyl hexanoate, ethyl octanoate, ethyl palmitate, (Z)-6-(ethylthiomethyl)benzene, eugenol, glucose, heptanoic acid, 2-heptanone, hexanal, hexanamide, hexanedioic acid, hexanoic acid (hexoic acid), 1-hexanol, 3-hydroxy-2-butanone, lauric acid, limonene, linoleic acid, 2-methylbutanoic acid, 3-methyl-2-buten-1-ol, 3-methyl-3-buten-1-ol, methyl decanoate, methyl elaidate, methyl hexanoate, methyl 3-methylthio-propanoate, methyl octanoate, methyl oleate, methyl palmitate, 2-methylpropanoic acid, 3-methylthiopropanoic acid, myristic acid, nonanoic acid, octanoic acid (octoic acid), oleic acid, palmitic acid, potassium, scopoletin, undecanoic acid, (Z,Z)-2,5-undecadien-1-ol, and vomifol; (from the roots):

anthraquinones, asperuloside (rubichloric acid), damnacanthal, glycosides, morindadiol, morindine, morindone, mucilaginous matter, nor-damnacanthal, rubiadin, rubiadin monomethyl ether, resins, soranjidiol, sterols, and trihydroxymethyl anthraquinone-monomethyl ether; (from the root bark): alizarin, chlororubin, glycosides (pentose, hexose), morindadiol, morindanigrine, morindine, morindone, resinous matter, rubiadin monomethyl ether, and soranjidiol; (from the wood): anthragallol-2,3-dimethylether; (from the tissue culture): damnacanthal, lucidin, lucidin-3-primeveroside, and morindone-6beta-primeveroside; (from the plant): alizarin, alizarin-alpha-methyl ether, anthraquinones, asperuloside, hexanoic acid, morindadiol, morindone, morindogenin, octanoic acid, and ursolic acid.

Recently, as mentioned, many health benefits have been discovered stemming from the use of products containing *Morinda citrifolia*. One benefit of *Morinda citrifolia* is found in its ability to isolate and produce Xeronine, which is a relatively small alkaloid physiologically active within the body. Xeronine occurs in practically all healthy cells of plants, animals and microorganisms. Even though *Morinda citrifolia* has a negligible amount of free Xeronine, it contains appreciable amounts of the precursor of Xeronine, called Proxeronine. Further, *Morinda citrifolia* contains the inactive form of the enzyme Proxeronase which releases Xeronine from Proxeronine. A paper entitled, "The Pharmacologically Active Ingredient of Noni" by R. M. Heinicke of the University of Hawaii, indicates that *Morinda citrifolia* is "the best raw material to use for the isolation of xeronine," because of the building blocks of Proxeronine and Proxeronase. These building blocks aid in the isolation and production of Xeronine within the body. The function of the essential nutrient Xeronine is fourfold.

First, Xeronine serves to activate dormant enzymes found in the small intestines. These enzymes are critical to efficient digestion, calm nerves, and overall physical and emotional energy.

Second, Xeronine protects and keeps the shape and suppleness of protein molecules so that they may be able to pass through the cell walls and be used to form healthy tissue. Without these nutrients going into the cell, the cell cannot perform its job efficiently. Without Proxeronine to produce Xeronine our cells, and subsequently the body, suffer.

Third, Xeronine assists in enlarging the membrane pores of the cells. This enlargement allows for larger chains of peptides (amino acids or proteins) to be admitted into the cell. If these chains are not used they become waste.

Fourth, Xeronine, which is made from Proxeronine, assists in enlarging the pores to allow better absorption of nutrients.

Each tissue has cells which contain proteins which have receptor sites for the absorption of Xeronine. Certain of these proteins are the inert forms of enzymes which require absorbed Xeronine to become active. Thus Xeronine, by converting the body's procollagenase system into a specific protease, quickly and safely removes the dead tissue from skin. Other proteins become potential receptor sites for hormones after they react with Xeronine. Thus the action of *Morinda citrifolia* in making a person feel well is probably caused by Xeronine converting certain brain receptor proteins into active sites for the absorption of the endorphin, the well being hormones. Other proteins form pores through membranes in the intestines, the blood vessels and other body organs. Absorbing Xeronine on these proteins changes the shape of the pores and thus affects the passage of molecules through the membranes.

Because of its many benefits, *Morinda citrifolia* has been known to provide a number of anecdotal effects in individuals having cancer, arthritis, headaches, indigestion, malignancies, broken bones, high blood pressure, diabetes, pain, infection, asthma, toothaches, blemishes, immune system failure, and others.

The compositions containing *Morinda citrifolia* may be in a form suitable for oral use, for example, as tablets, or lozenges, aqueous or oily suspensions, dispersible powders or granules, emulsions, syrups or elixirs. Compositions intended for oral use may be prepared according to any method known in the art for the manufacture of *Morinda citrifolia* compositions and such compositions may contain one or more agents selected from the group consisting of sweetening agents, flavoring agents, coloring agents and preserving agents. Tablets contain *Morinda citrifolia* in admixture with non-toxic pharmaceutically acceptable excipients which are suitable for the manufacture of tablets. These excipients may be for example, inert diluents, granulating and disintegrating agents, binding agents, and lubricating agents. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Aqueous suspensions contain the *Morinda citrifolia* in admixture with excipients suitable for the manufacture of aqueous suspensions. Such excipients are suspending agents, for example, sodium carboxymethyl-cellulose, methylcellulose, hydroxy-propylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitor monooleate, or condensation products of ethylene oxide with partial esters derived from fatty acids and hexitol anhydrides, for example polyethylene sorbitan monooleate.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

Favorably, this invention provides a method of treating osteoarthritis comprising a *Morinda citrifolia*-based formulation without any significant tendency to cause gastric or other side effects.

*Morinda citrifolia*-Based Naturaceutical Formulations and Methods of Treating Osteoarthritis The present invention features a unique formulation and method of administering the same to treat osteoarthritis, or rather advances treatment of osteoarthritis by providing a naturaceutical composition or treatment formulated with one or more processed *Morinda citrifolia* products derived from the Indian Mulberry plant. The *Morinda citrifolia* product is incorporated into various carriers or naturaceutical compositions suitable for in vivo treatment of a patient. For instance, the naturaceutical formulation may be ingested orally, introduced through an intravenous injection or feeding, or otherwise internalized as is appropriate and directed.

As mentioned, osteoarthritis, also called degenerative joint disease, is the most common type of arthritis, which is essentially an inflammation of the joints. Osteoarthritis is associated with a breakdown of cartilage in joints and commonly occurs in the hips, knees, and spine. Osteoarthritis can also affect the finger joints, the joint at the base of the thumb, and the joint at the base of the big toe. Osteoarthritis causes the cartilage in a joint to become stiff and lose its elasticity, making it more susceptible to damage. Cartilage is a firm, rubbery protein substance that covers the ends of bones in normal joints. Its main function is to reduce friction in the joints and serve as a "shock absorber." The shock-absorbing quality of normal cartilage comes from its ability to change shape when compressed. Cartilage can change shape because it contains more than 70 percent water, which can be redistributed with movement. And, because cartilage does not contain nerves, you do not feel pain when these changes in shape occur. Over time, the cartilage may wear away in some areas, greatly decreasing its ability to act as a shock-absorber. As the cartilage wears away, tendons and ligaments stretch, causing pain. If the condition worsens, the bones could rub against each other. Some of the symptoms of osteoarthritis are aching and soreness in the joints, especially with movement, pain after overuse or after long periods of inactivity, and bony enlargements in the middle and end joints of the fingers.

The naturaceutical composition of the present invention comprises one or more processed *Morinda citrifolia* products present in an amount by weight between about 0.01 and 100 percent by weight, and preferably between 0.01 and 95 percent by weight. Several embodiment of formulations are provided below. However, these are only intended to be exemplary as one ordinarily skilled in the art will recognize other formulations or compositions comprising the processed *Morinda citrifolia* product.

The processed *Morinda citrifolia* product is the active ingredient or contains one or more active ingredients, such as Quercetin and Rutin, and others, for effectuating the inhibition and prevention of protein and cartilage degeneration within the joints of a mammal resulting in osteoarthritis, as well as for treating or relieving existing osteoarthritis by providing cell enhancing nutrients to degenerated cartilage. Active ingredients may be extracted out using various alcohol or alcohol-based solutions, such as methanol, ethanol, and ethyl acetate, and other alcohol-based derivatives using any known process in the art. The active ingredients of Quercetin and Rutin are present in amounts by weight ranging from 0.01–10 percent of the total formulation or composition. These amounts may be concentrated as well into a more potent concentration in which they are present in amounts ranging from 10 to 100 percent.

The processed *Morinda citrifolia* product may be formulated with various other ingredients to produce various compositions, such as a naturaceutical composition, a topical dermal composition, a systemically administered composition, or others. The ingredients to be utilized in a naturaceutical composition are any that are safe for introduction into the body of a mammal, and particularly a human, and may exist in various forms, such as liquids, tablets, lozenges, aqueous or oily solutions, dispersible powders or granules, emulsions, syrups, elixirs, etc.

In one exemplary embodiment, the present invention further features a method of administering a naturaceutical composition to a mammal for the treatment of osteoarthritis and its related conditions. The method comprises the steps of (a) formulating a naturaceutical composition comprising in part a processed *Morinda citrifolia* product present in an amount between about 0.01 and 100 percent by weight, and preferably 0.1 to 95 percent by weight, wherein the composition also comprises a carrier, such as water or purified water, and other natural or artificial ingredients; (b) administering the naturaceutical composition into the body such that the Morinda citrifolia is sufficiently internalized and concentrated within the colon; (c) repeating the above steps as often as necessary to provide an effective amount of Morinda citrifolia to the tissues of the colon.

In one exemplary embodiment, the step of administering the naturaceutical composition into the body comprises ingesting the composition orally through one of several means. Specifically, the naturaceutical composition may be formulated as a liquid, gel, solid, or some other type that would allow the composition to be quickly digested and concentrated within the colon. It is important to note that the step of administering the naturaceutical composition should be carried out in an effective manner so that the greatest concentration of naturaceutical composition is allowed to be internalized. For the naturaceutical composition to take effect, it must be sufficiently internalized into the body where it may then begin to act upon the cartilage in the joints. Moreover, since the naturaceutical composition will most likely be consumed orally, it may contain one or more agents selected from the group consisting of sweetening agents, flavoring agents, coloring agents, preserving agents, and other medicinal agents as directed.

In another exemplary embodiment, the step of administering the naturaceutical composition into the body comprises applying a topical dermal composition, comprising processed Morinda citrifolia as at least one existing ingredient in the composition, to the skin adjacent the affected or arthritic area. The ingredients to be utilized in a topical dermal composition are also any that are safe for internalizing into the body of a mammal and may exist in various forms, such as gels, lotions, creams, ointments, etc., each comprising one or more carrier agents.

In still another exemplary embodiment, the step of administering the naturaceutical composition into the body comprises systemically introducing a processed Morinda citrifolia product-based formulation into the body via any known means in the art. The ingredients for the systemically administered formulation may also comprise any commonly known in the art.

In addition, the step of administering the naturaceutical composition may include injecting the composition into the body using an intravenous pump. This technique is advantageous as it would allow the composition to be localized in the area where it would have the most effect, or the area that would provide for the greatest concentration of the naturaceutical composition—within an arthritic region.

The treatment of osteoarthritis by inhibiting degeneration of cartilage tissue results from the affect of these processed Morinda citrifolia products, and/or the active ingredients found therein, namely Quercetin, Rutin, Xeronine, and the building blocks to Xeronine—Proxeronase and Proxeronine, on the cartilage tissue and the cells therein. Specifically, the processed Morinda citrifolia products, whether they be in the form of fruit juice, puree juice, dietary fiber, oil, etc., function to convert receptor proteins and other enzymes into active sites for better and more efficient absorption of various nutrients. The processed Morinda citrifolia products also assist other proteins in forming pores through membranes in the blood vessels and other organs in the body. As these products are internalized into the body through the introduction of the naturaceutical formulation or topical dermal composition in which they are contained, they are absorbed by the various proteins in the body and go to work at facilitating the change in shape of the pores, thus positively or beneficially affecting the passage of molecules through the membranes. These unique affects specifically function to reduce and inhibit degeneration of cartilage tissue, which is the primary factor in developing osteoarthritis. As such, it can be said that the present invention further comprises a method for normalizing or improving the passage of molecules and/or hormones through membranes in the cartilage.

In one exemplary embodiment, the naturaceutical composition is administered by taking between 1 teaspoon and 2 oz., and preferably 2 oz., of the naturaceutical composition every two hours each day, or at least twice a day. Also, the naturaceutical composition is to be taken on an empty stomach, meaning at a period of time at least two hours prior to consumption of any food or drink. Following this, the naturaceutical composition actively impacts the cartilage tissue within the joints, thereby inhibiting the degeneration of the cartilage tissue and combating the effects of osteoarthritis. Of course, one ordinarily skilled in the art will recognize that the amount of composition and frequency of use may vary from individual to individual.

The following tables illustrate or represent some of the preferred formulations or compositions contemplated by the present invention. As stated, these are only intended as exemplary embodiments and are not to be construed as limiting in any way.

| Ingredients | Percent by Weight |
| --- | --- |
| Formulation One | |
| Morinda citrifolia puree juice or fruit juice | 100% |
| Formulation Two | |
| Morinda citrifolia fruit juice | 85–99.99% |
| water | 0.1–15% |
| Formulation Three | |
| Morinda citrifolia fruit juice | 85–99.99% |
| non-Morinda citrifolia-based fruit juices | 0.1–15% |
| Formulation Four | |
| Morinda citrifolia fruit juice | 50–90% |
| water | 0.1–50% |
| non-Morinda citrifolia-based fruit juices | 0.1–30% |
| Formulation Five | |
| Morinda citrifolia puree juice | 85–99.9% |
| water | 0.1–15% |
| Formulation Six | |
| Morinda citrifolia puree juice | 85–99.9% |
| non-Morinda citrifolia-based fruit juices | 0.1–15% |
| Formulation Seven | |
| Morinda citrifolia puree juice | 50–90% |
| water | 0.1–50% |
| non-Morinda citrifolia-based fruit juices | 0.1–30% |
| Formulation Eight | |
| Morinda citrifolia dietary fiber | 0.1–30% |
| water | 1–99.9% |
| non-Morinda citrifolia-based fruit juices | 1–99.9% |
| Formulation Nine | |
| Morinda citrifolia dietary fiber | 0.1–30% |
| water | 1–99.9% |
| Morinda citrifolia fruit juice or puree juice | 1–99.9% |
| Formulation Ten | |
| Morinda citrifolia oil | 0.1–30% |

-continued

| Ingredients | Percent by Weight |
|---|---|
| carrier medium | 70–99.9% |
| other ingredients | 1–95% |
| Formulation Eleven | |
| *Morinda citrifolia* product | 10–80% |
| carrier medium | 20–90% |
| Formulation Twelve | |
| *Morinda citrifolia* product | 5–80% |
| carrier medium | 20–95% |
| Formulation Thirteen | |
| *Morinda citrifolia* oil or oil extract | 0.1–20% |
| carrier medium | 20–90% |
| Formulation Fourteen | |
| *Morinda citrifolia* puree juice or fruit Juice | 0.1–80% |
| *Morinda citrifolia* oil | 0.1–20% |
| carrier medium | 20–90% |
| Formulation Fifteen | |
| *Morinda citrifolia* puree juice concentrate or fruit juice concentrate | 100% |
| Formulation Sixteen | |
| *Morinda citrifolia* fruit juice concentrate or puree juice concentrate | 85–99.99% |
| water | 0.1–15% |

In another exemplary embodiment, a person suffering from osteoarthritis as described above takes, or is administered, at least one (1) ounce of Formulation One in the morning on an empty stomach, and at least one (1) ounce at night on an empty stomach, just prior to retiring to bed. In one example, which is not meant to be limiting in any way, the beneficial *Morinda Citrifolia* is processed into Tahitian Noni® juice manufactured by Morinda, Incorporated of Orem, Utah.

As stated above, one exemplary embodiment of the present invention features a method for introducing a topical dermal composition of formulation to a region of the body affected by osteoarthritis. This method essentially comprises the application of a topical dermal composition to the skin of the patient, wherein the composition is absorbed or internalized into the body. Several embodiments of the topical dermal composition comprising various different ingredients are contemplated for use herein, with each embodiment comprising one or more forms of a processed *Morinda citrifolia* product as taught and explained herein and a carrier agent or medium.

In one exemplary embodiment, the topical dermal composition comprises the ingredients of: a processed *Morinda citrifolia* product present in an amount by weight between about 10–80 percent; and a carrier medium present in an amount by weight between about 20–90 percent.

In this embodiment, the processed *Morinda citrifolia* product may comprise one or more of processed *Morinda citrifolia* fruit juice, processed *Morinda citrifolia* puree juice, processed *Morinda citrifolia* dietary fiber, and/or processed *Morinda citrifolia* oil or oil extract.

In another exemplary embodiment, the internal composition comprises the ingredients of: processed *Morinda citrifolia* fruit juice or puree juice present in an amount by weight between about 0.1–80 percent; processed *Morinda citrifolia* oil present in an amount by weight between about 0.1–20 percent; and a carrier medium present in an amount by weight between about 20–90 percent. *Morinda citrifolia* puree juice or fruit juice may also be formulated with a *Morinda citrifolia* dietary fiber product in similar concentrations.

The carrier medium in the topical dermal composition may comprise any ingredient capable of being safely introduced into the body of a mammal, and that is also capable of providing the carrying medium to the processed *Morinda citrifolia* product. Specific carrier mediums formulations are well known in the art and not described in detail herein. The purpose of the carrier medium is as stated, to provide a means to embody the processed *Morinda citrifolia* product within the internal composition that is capable of being introduced into the body, and particularly, into an arthritic area or region.

The present invention further features taking an osteoarthritis medication concurrently with the naturaceutical formulation. Taking or administering the naturaceutical formulation, comprising one form or another of a processed *Morinda citrifolia* product as taught and described herein, concurrently with an osteoarthritis medication functions to enhance the relief potential for the patient by increasing or enhancing the efficacy of the osteoarthritis medication, as well as providing the same benefits and advantages to the patient that are obtained directly from the naturaceutical formulation. Osteoarthritis medications used to treat osteoarthritis and relieve pain are well known and can be grouped into three different categories—symptomatic relief, abortive therapy, and preventive therapy. Symptomatic relief medications are used to relieve symptoms associated with existing osteoarthritis. Abortive medications are used to block the pain. Preventive medications are used to reduce some of the factors that contribute to osteoarthritis.

Cyclooxygenase-1 and 2 (or Cox-1 and Cox-2) Implications

Recent studies show that the present invention *Morinda citrifolia*-based formulations and compositions described herein have beneficial cyclooxygenase-1 and 2 (COX-1 and COX-2) implications. COX-1 and COX-2, are known to be involved in prostaglandin synthesis. COX-1 generates prostaglandins that are involved in the protection of gastrointestinal mucosa, while COX-2 generates prostaglandins that mediate inflammation and pain in sites throughout the body. Selective COX-2 inhibitors may therefore relieve pain associated with osteoarthritis without deleterious effects on gastrointestinal mucosa. The present invention formulations discussed herein are capable of selectively inhibiting COX-2, or as functioning as selective COX-2 inhibitors.

One embodiment of the present invention uses a selective COX-2 inhibitor as an anti-inflammatory agent where use of the selective COX-2 inhibitor does not result in the unpleasant side effects associated with NSAIDs and selective COX-2 inhibition drugs presently available.

The present invention provides a method of treating various diseases and ailments, which comprises administering to a mammal a therapeutically effective amount of a naturaceutical formulation comprising one or more processed *Morinda citrifolia* products. The naturaceutical comprising the processed *Morinda citrifolia* product is generally administered in the form of a juice, oil, capsule or as an ingredient in another food product. An advantage of using processed *Morinda citrifolia* is that treatment may be carried out without causing gastric side effects that can occur by using NSAIDs for prolonged periods.

In a one exemplary embodiment, the naturaceutical formulation comprises processed *Morinda citrifolia* fruit juice or puree juice (in dilute or concentrate form), which has been discovered to have selective COX-2 inhibitor characteristics, and is administered orally. The precise mechanism by which processed *Morinda citrifolia* selectively inhibits COX-2 is not known. A preferred method of the present invention comprises the consumption of processed *Morinda citrifolia* juice in therapeutic amounts.

In another exemplary embodiment, the present invention features one or more pharmaceutical compositions, such as a topical dermal composition, comprising one or more processed *Morinda citrifolia* products and a carrier medium for inhibiting the production of the prostaglandins by COX-2 and treating osteoarthritis and its associated conditions. The pharmaceutical composition could take the form of a tablet or capsule, lotions, creams, solutions, or be included as an ingredient in another food product.

The following examples set forth and present the effects of *Morinda citrifolia* on healthy and degenerating cartilage, as well as the preventative and treatment effects of *Morinda citrifolia* against osteoarthritis. These examples are not intended to be limiting in any way, but are merely illustrative of the benefits and advantageous, as well as the remedial effects, of *Morinda citrifolia* on osteoarthritis.

EXAMPLE ONE

In the present example, a patient experiencing and diagnosed with osteoarthritis desires to treat the degenerative disease with a non-prescription, over-the-counter remedy or preparation. Thus, to treat the osteoarthritis, an individual is given an identified, prescribed amount of a naturaceutical composition to consume orally, wherein the naturaceutical comprises 100% processed *Morinda citrifolia* fruit juice. The naturaceutical is administered in a safe, pre-determined amount and is administered intermittently a safe, pre-determined number of times, thus alleviating the pain and other symptoms associated with osteoarthritis, and inhibiting further degeneration of cartilage tissue. The *Morinda citrifolia*-based naturaceutical is consumed by the patient on an empty stomach.

The present invention may be embodied in other specific forms without departing from its spirit of essential characteristics. The described embodiments are to be considered in all respects only al illustrative and not restrictive. The scope of the invention is, therefore, indicated by the appended claims, rather than by the foregoing description. All changes which come within the meaning and range of equivalency of the claims are to be embraced within their scope.

The invention claimed is:

1. A method for treating pain associated with osteoporosis said method comprising the steps of:
   introducing an internal composition to said cartilage region, said internal composition comprising the ingredients of:
   processed *Morinda citrifolia* product selected from one of a fruit juice product and a puree juice produce, said processed *Morinda citrifolia* product present in an amount by weight between about 0.1–80 percent;
   processed *Morinda citrifolia* oil present in an amount by weight between about 0.1–20 percent; and
   a carrier medium present in an amount by weight between about 20–90 percent.

2. The method of claim 1, wherein said step of introducing an internal composition is done intravenously.

3. The method of claim 1, wherein said step of introducing an internal composition is done transdermally.

4. The method of claim 1, wherein said step of introducing an internal composition is done systemically.

* * * * *